United States Patent
Brandl et al.

(10) Patent No.: US 12,056,873 B2
(45) Date of Patent: Aug. 6, 2024

(54) METHOD AND SYSTEM FOR AUTOMATICALLY ANALYZING PLACENTA INSUFFICIENCY IN A CURVED TOPOGRAPHICAL ULTRASOUND IMAGE SLICE

(71) Applicant: GE Precision Healthcare LLC, Wauwatosa, WI (US)

(72) Inventors: Helmut Brandl, Pfaffing (AT); Christian Perrey, Mondsee (AT)

(73) Assignee: GE PRECISION HEALTHCARE LLC, Waukesha, WI (US)

(*) Notice: Subject to any disclaimer, the term of this patent is extended or adjusted under 35 U.S.C. 154(b) by 412 days.

(21) Appl. No.: 17/557,794

(22) Filed: Dec. 21, 2021

(65) Prior Publication Data

US 2023/0196554 A1    Jun. 22, 2023

(51) Int. Cl.
*G06T 7/00* (2017.01)
*A61B 8/00* (2006.01)
(Continued)

(52) U.S. Cl.
CPC .......... *G06T 7/0012* (2013.01); *A61B 8/0866* (2013.01); *A61B 8/461* (2013.01);
(Continued)

(58) Field of Classification Search
CPC . G06T 7/0012; G06T 7/11; G06T 7/90; G06T 2207/10024; G06T 2207/10132;
(Continued)

(56) References Cited

U.S. PATENT DOCUMENTS 6,352,509 B1 * 3/2002 Kawagishi ............ A61B 8/065
600/443
6,464,640 B1 * 10/2002 Guracar ............ G01S 7/52074
600/453
(Continued)

FOREIGN PATENT DOCUMENTS

EP       0797106 B1    4/2006

OTHER PUBLICATIONS

Reijnders, et al., "New imaging markers for preconceptional and first-trimester utero-placental vascularization," Placenta, vol. 61, 2018, pp. 96-102.

*Primary Examiner* — Phuoc Tran
(74) *Attorney, Agent, or Firm* — McAndrews, Held & Malloy, Ltd.; Daniel Bissing; David Bates

(57) ABSTRACT

A system and method for automatically analyzing placenta insufficiency in a curved topographical ultrasound image slice is provided. The method includes acquiring, by an ultrasound system, an ultrasound volume of a placental anatomy section, the ultrasound volume comprising color Doppler information. The method includes extracting, by at least one processor of the ultrasound system, a topographical ultrasound image slice at a distance below an inner surface of the placental anatomy section. The topographical ultrasound image slice is curved in all three dimensions and includes the color Doppler information. The method includes analyzing, by the at least one processor, the color Doppler information of the topographical ultrasound image slice to generate perfusion data information. The method includes causing, by the at least one processor, a display system to present the topographical ultrasound image slice with the perfusion data information.

20 Claims, 8 Drawing Sheets

(51) Int. Cl.
*A61B 8/08* (2006.01)
*G06T 7/11* (2017.01)
*G06T 7/90* (2017.01)

(52) U.S. Cl.
CPC ............ *A61B 8/488* (2013.01); *A61B 8/5223* (2013.01); *A61B 8/523* (2013.01); *G06T 7/11* (2017.01); *G06T 7/90* (2017.01); *G06T 2207/10024* (2013.01); *G06T 2207/10132* (2013.01); *G06T 2207/20021* (2013.01); *G06T 2207/20096* (2013.01); *G06T 2207/30104* (2013.01)

(58) Field of Classification Search
CPC .......... G06T 2207/30104; A61B 8/488; A61B 8/5223; A61B 8/483; A61B 8/0891; A61B 8/14; A61B 8/5207; G06N 3/08; G16H 30/00
See application file for complete search history.

(56) References Cited

U.S. PATENT DOCUMENTS

| | | |
|---|---|---|
| 9,687,212 B2 | 6/2017 | Hamada et al. |
| 9,955,941 B2 * | 5/2018 | Rafter .................... A61B 8/481 |
| 9,999,405 B2 | 6/2018 | Pintoffl et al. |
| 2014/0160114 A1 | 6/2014 | Stevenson et al. |

* cited by examiner

METHOD AND SYSTEM FOR AUTOMATICALLY ANALYZING PLACENTA INSUFFICIENCY IN A CURVED TOPOGRAPHICAL ULTRASOUND IMAGE SLICE

FIELD

Certain embodiments relate to ultrasound imaging. More specifically, certain embodiments relate to a method and system for automatically analyzing placenta insufficiency by extracting a topographical ultrasound image slice curved in all three dimensions and comprising color Doppler information, which is automatically analyzed to generate perfusion data information displayed with the topographical slice at a display system.

BACKGROUND

Ultrasound imaging is a medical imaging technique for imaging organs and soft tissues in a human body. Ultrasound imaging uses real time, non-invasive high frequency sound waves to produce a series of two-dimensional (2D) and/or three-dimensional (3D) images.

In obstetrical ultrasound, several structures inside the uterine cavity are of specific interest, such as the fetus, umbilical cord, placenta, and the like. Different modes of volume rendering are applied to illustrate these structures of the uterine cavity. Intrauterine growth restriction (IUGR) is when a fetus is not as big as would be expected at a particular gestational age. Placental infarct results from the interruption of blood supply to a part of the placenta, causing its cells to die. Placental infarct may have a serious impact on the fetus, such as the IUGR and vascular abnormalities. Placental infarct is difficult to diagnose with ultrasound because the placenta has an irregular shape in all directions. Typically, due to the irregular shape of the placenta, multiple planar slices are extracted from an ultrasound volume to visualize a perfusion status of the placenta below its surface, which is time consuming and difficult for less experienced users to analyze.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for automatically analyzing placenta insufficiency in a curved topographical ultrasound image slice, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
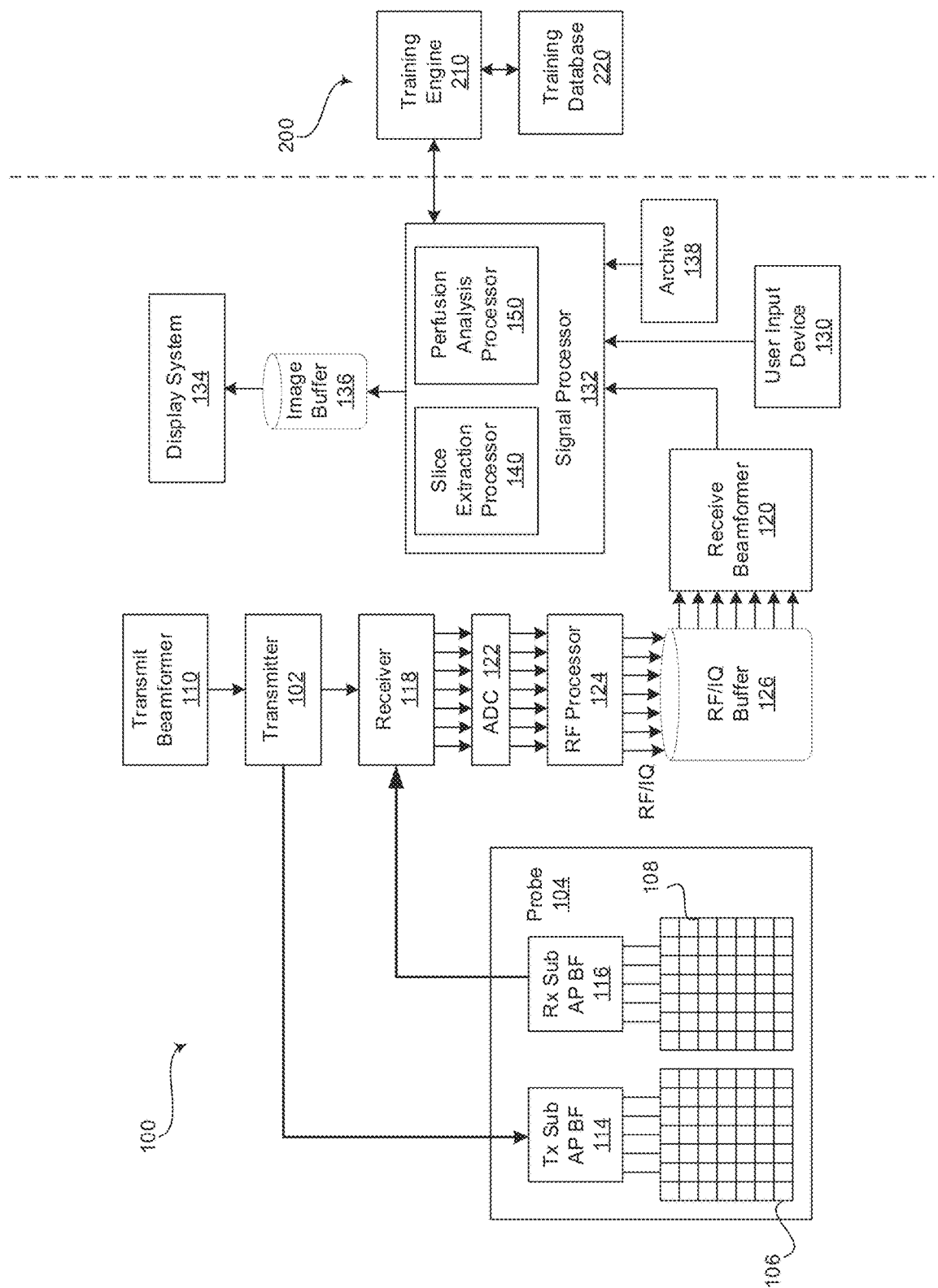
FIG. 1 is a block diagram of an exemplary ultrasound system that is operable to automatically analyze placenta insufficiency in a curved topographical ultrasound image slice, in accordance with various embodiments.

Certain embodiments may be found in a method and system for automatically analyzing placenta insufficiency in a curved topographical ultrasound image slice. Aspects of the present disclosure have the technical effect of automatically extracting a topographical ultrasound image slice that follows at a specified distance below an inner surface of an anatomy, such as a placenta. Various embodiments have the technical effect of providing tools manipulable to manually define a curvature of a topographical ultrasound image slice to be extracted. Certain embodiments have the technical effect of providing a volume rendering of a topographical ultrasound image slice curved in all three dimensions. Aspects of the present disclosure have the technical effect of automatically generating perfusion data information by analyzing color Doppler information of a curved topographical ultrasound image slice. Certain embodiments have the technical effect of presenting a curved topographical ultrasound image slice with automatically generated perfusion data information.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising", "including", or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, Contrast Enhanced Ultrasound (CEUS), and/or sub-modes of B-mode and/or CF such as Harmonic Imaging, Shear Wave Elasticity Imaging (SWEI), Strain Elastography, TVI, PDI, B-flow, MVI, UGAP, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphic Processing Unit (GPU), DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to automatically analyze placenta insufficiency in a curved topographical ultrasound image slice, in accordance with various embodiments. Referring to FIG. 1, there is shown an ultrasound system 100 and a training system 200. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as a placenta, a fetus, a heart, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, select measurements, manipulate tools for defining ultrasound slice curvature, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise a slice extraction processor 140 and a perfusion analysis processor 150. The signal processor 132 may be capable of receiving input information from a user input device 130 and/or archive 138, generating an output displayable by a display system 134, and manipulating the output in response to input information from a user input device 130, among other things. The signal processor 132, slice extraction processor 140, and perfusion analysis processor 150 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a slice extraction processor 140 that comprises suitable logic, circuitry, interfaces and/or code that may be operable to extract a topographical slice, curved in all three dimensions and having color Doppler information, from an ultrasound volume comprising color Doppler information of a placental anatomy section. The slice extraction processor 140 may be configured to provide tools presented with ultrasound planes (e.g., A-plane, B-plane, and/or C-plane) of the volume at the display system 134 and manipulable to manually select a curvature of a topographical slice to be extracted from the ultrasound volume. For example, the slice extraction processor 140 may present curvature line tools overlaid on an A-plane and a B-plane of an ultrasound volume. The curvature line tools may be dragged and/or otherwise manipulated to set the topographical slice curvature. The slice extraction processor 140 may be configured to extract and render a topographical ultrasound slice curved in all three dimensions based on the manipulated positioning of the curvature line tools and a defined slice thickness. Additionally and/or alternatively, the slice extraction processor 140 may include image analysis algorithms, artificial intelligence algorithms, one or more deep neural networks (e.g., a convolutional neural network) and/or may utilize any suitable form of image analysis techniques or machine learning processing functionality configured to identify an inner surface of a placental anatomy section depicted in the ultrasound volume. The slice extraction processor 140 may be configured to automatically extract a topographical ultrasound slice curved in all three dimensions from the ultrasound volume, the topographical slice following a specified distance or depth (e.g., 5 millimeters or any suitable distance/depth) below the identified inner surface of the placental anatomy section depicted in the ultrasound volume. The slice extraction processor 140 may be configured to extract and render a topographical ultrasound slice curved in all three dimensions based on the identified inner surface, the specified distance, and a defined slice thickness (e.g., between 1-5 millimeters). The slice extraction processor 140 may be configured to provide the rendered, curved topographical ultrasound image slice to the perfusion analysis processor 150. The slice extraction processor 140 may additionally and/or alternatively present the rendered, curved topographical ultrasound image slice at the display system 134 and/or store the rendered, curved topographical ultrasound image slice at archive 138 and/or any suitable data storage medium.

The slice extraction processor 140 may comprise suitable logic, circuitry, interfaces and/or code that may be operable to automatically identify an inner surface of a placental anatomy section depicted in the ultrasound volume. In various embodiments, the slice extraction processor 140 may be provided as a deep neural network that may be made up of, for example, an input layer, an output layer, and one or more hidden layers in between the input and output layers. Each of the layers may be made up of a plurality of processing nodes that may be referred to as neurons. For example, the slice extraction processor 140 may include an input layer having a neuron for each pixel or a group of pixels from an ultrasound volume of a placental anatomy section. The output layer may have neurons corresponding to an inner surface of the placental anatomy section and/or any suitable anatomical structures. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The processing performed by the slice extraction processor 140 deep neural network (e.g., convolutional neural network) may identify an inner surface of a placental anatomy section depicted in an acquired ultrasound volume with a high degree of probability. The distance below the inner surface of the placental anatomy section may be a default distance and/or a distance selectable by an ultrasound operator via the user input device 130. The thickness of the curved topographical ultrasound image slice to be extracted may be a default thickness and/or a thickness selectable by an ultrasound operator via the user input device 130. In various embodiments, the thickness may be in a selectable range of 1-5 millimeters. The slice extraction processor 140 may be configured to extract and render a topographical ultrasound slice curved in all three dimensions based on the identified inner surface, the specified distance, and the defined slice thickness.

Figure 2:
FIG. 2 is a screenshot of an exemplary A-plane ultrasound image view of a placenta having a tool manipulable to set a curvature of a topographical ultrasound image slice, in accordance with various embodiments.
Figure 3:
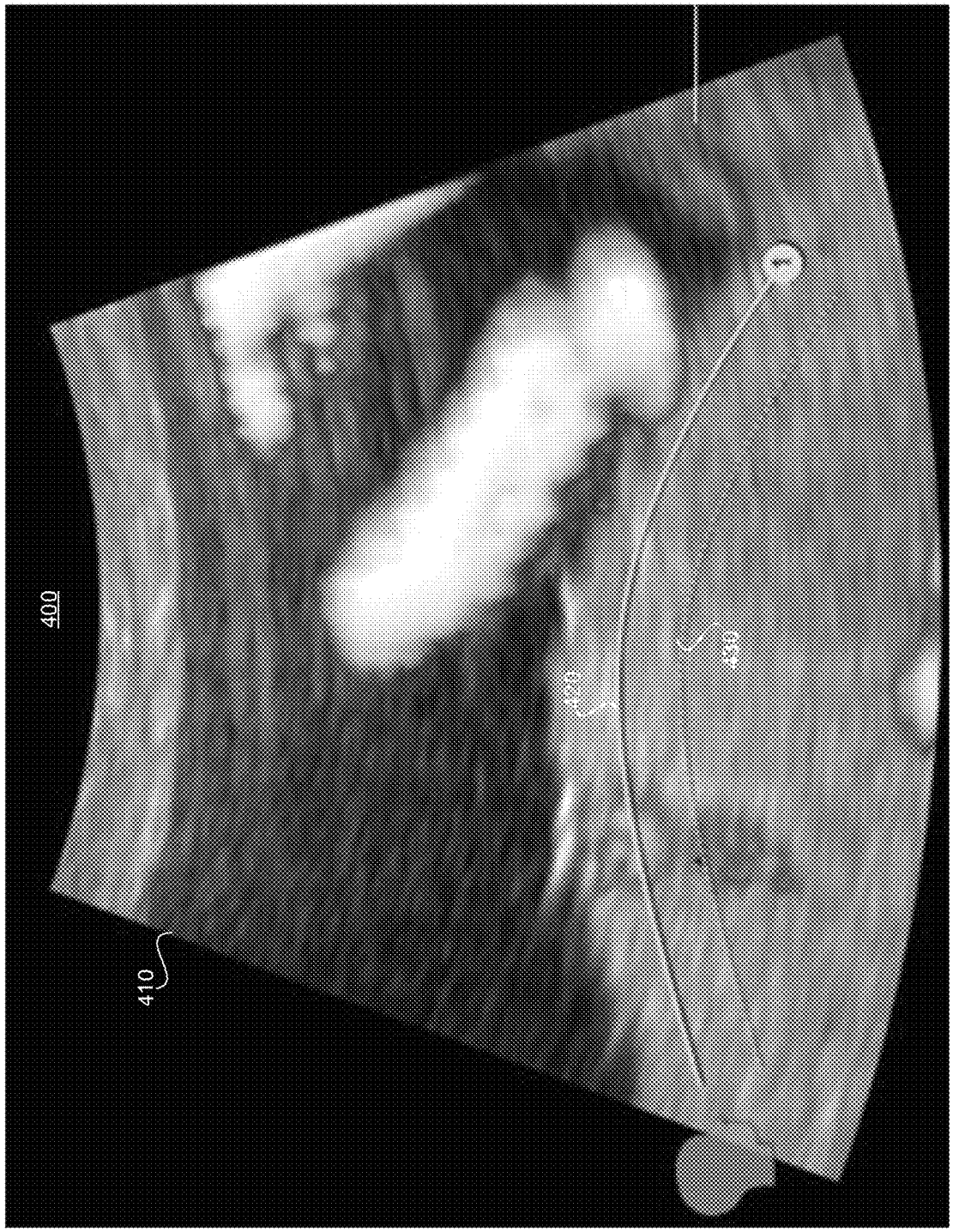
FIG. 3 is a screenshot of an exemplary B-plane ultrasound image view of a placenta having a tool manipulable to set a curvature of a topographical ultrasound image slice, in accordance with various embodiments.

FIG. 2 is a screenshot 300 of an exemplary A-plane ultrasound image view 310 of a placenta having a tool 320 manipulable to set a curvature of a topographical ultrasound image slice, in accordance with various embodiments. FIG. 3 is a screenshot of an exemplary B-plane ultrasound image view 410 of a placenta having a tool 420 manipulable to set a curvature of a topographical ultrasound image slice, in accordance with various embodiments. Referring to FIGS. 2 and 3, screenshots 300, 400 of an exemplary A-plane ultrasound image view 310 and B-plane ultrasound image view 410 are shown. The A-plane ultrasound image view 310 and B-plane ultrasound image view 410 are superimposed with manipulable tools 320, 420 configured to select a curvature of a topographical ultrasound slice to be extracted. The tools 320, 420 may be lines overlaid on the image views 310, 410 that may be selected and dragged to alter a position of the tool 320, 420 and the curvature of the tool 320, 420. For example, an ultrasound operator may operate the user input device 130 to select a point along the tool 320, 420 and drag the tool 320, 420 to adjust the curvature of the tool 320, 420. The curvature of the manipulable tool 320 in the A-plane ultrasound image view 310 and the curvature of the manipulable tool 420 in the B-plane ultrasound image view 410 may be combined by the slide extraction processor 140 to determine the curvature of the topographical ultrasound image slice to extract in all three dimensions. The A-plane ultrasound image view 310 and B-plane ultrasound image view 410 may also include an indication of a thickness 330, 430 of the topographical ultrasound image slice to be extracted. The slice thickness may be determined based on a thickness of the placental volume. The slice thickness may be a default thickness, a user selected thickness, and/or a slice thickness automatically determined by the slice extraction processor 140. For example, the slice extraction processor 140 may be configured to automatically set the slice thickness based on a thickness of the placental volume such that only placental tissue is encompassed within the extracted slice. The indication of the slice thickness 330, 430 may be selected or updated by an ultrasound operator via the user input device by moving the indication 330, 430, entering an updated slice thickness, or based on any suitable user selection. The indication of the slice thickness 330, 430 is configured to move synchronously with changes to the manipulable tools 320, 420.

Figure 4:
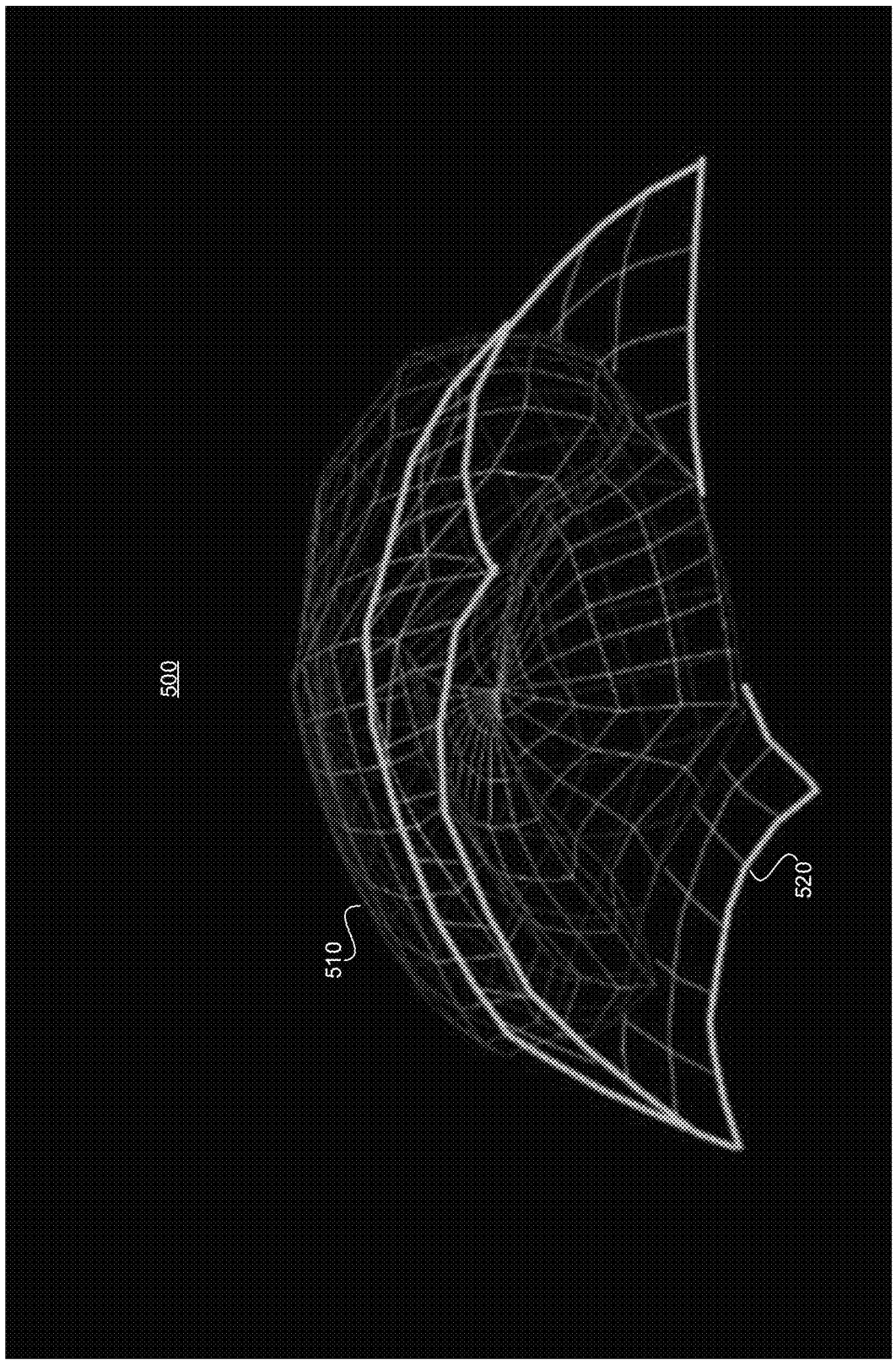
FIG. 4 is a display of an exemplary ultrasound slice curved in all three dimensions through an exemplary model of a placenta, in accordance with various embodiments.

FIG. 4 is a display 500 of an exemplary ultrasound slice 510 curved in all three dimensions through an exemplary model of a placenta 520, in accordance with various embodiments. Referring to FIG. 4, a model of an exemplary placenta 520 is shown having an ultrasound slice 520 that is curved in all three dimensions passing through the placenta model 510. The curvature of the ultrasound slice 520 may be automatically selected by the slice extraction processor 140 based on an identification of the placenta inner surface, a specified distance below the inner surface of the placenta, and a defined slice thickness. The defined slice thickness may be a default thickness, a user selected thickness, and/or a slice thickness automatically determined by the slice extraction processor 140. For example, the slice extraction processor 140 may be configured to automatically set the slice thickness based on a thickness of the volumetric model of the placenta 520 such that only placental tissue is encompassed within the extracted curved ultrasound image slice 510. Additionally and/or alternatively, the curvature of the ultrasound slice 520 may be manually selected by an ultrasound operator via the user input device 130 by interacting with the manipulable tools 320, 420 as shown in FIGS. 2 and 3.

Referring again to FIG. 1, the signal processor 132 may include perfusion analysis processor 150 that comprises suitable logic, circuitry, interfaces and/or code that may be operable to analyze color Doppler information of the topographical ultrasound image slice to generate perfusion data information. The perfusion data information may include segmented perfused areas larger than a pre-determined size threshold, an indication of whether a counted number of segmented perfused areas exceeds a pre-determined minimum, blood velocity measurements (e.g., peak absolute velocity, mean absolute velocity, ratio of peak positive to peak negative velocity, ratio of mean positive to mean negative velocity, and the like) in grid cells of a grid overlaid on a topographical ultrasound image slice, perfused area ratio measurements (e.g., ratio of perfused area to non-perfused area) in grid cells of a grid overlaid on a topographical ultrasound image slice, highlighting of low perfusion areas, and/or any suitable indication of low perfusion areas in a topographical ultrasound image slice.

The perfusion analysis processor 150 may include image analysis algorithms, artificial intelligence algorithms, one or more deep neural networks (e.g., a convolutional neural network) and/or may utilize any suitable form of image analysis techniques or machine learning processing functionality configured to segment perfused areas in a topographical ultrasound image slice. In various embodiments, the perfusion analysis processor 150 may be configured to segment only perfused areas that are larger than a pre-determined size threshold. In an exemplary embodiment, the perfusion analysis processor 150 may be provided as a deep neural network that may be made up of, for example, an input layer, an output layer, and one or more hidden layers in between the input and output layers. Each of the layers may be made up of a plurality of processing nodes that may be referred to as neurons. For example, the perfusion analysis processor 150 may include an input layer having a neuron for each pixel or a group of pixels from a topographical ultrasound image slice of a placental anatomy section having color Doppler information. The output layer may have neurons corresponding to segmented perfused areas of the placental anatomy section. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The processing performed by the perfusion analysis processor 150 deep neural network (e.g., convolutional neural network) may segment perfused areas of a placental anatomy section depicted in a topographical ultrasound image slice with a high degree of probability.

The perfusion analysis processor 150 may be configured to cause the display system 134 to present a rendering of the curved topographical ultrasound image slice having the segmented perfusion areas. In various embodiments, the segmented perfused areas may include only perfused areas that are larger than a pre-determined size threshold. The segmented perfused areas may be shown by outlining, highlighting, and/or any suitable indication of the segmented perfused areas. In various embodiments, the perfusion analysis processor 150 may be configured to count the segmented perfused areas presented on the curved topographical ultrasound image slice. The perfusion analysis processor 150 may be configured to provide an alert if the counted number of segmented perfused areas fails to exceed a pre-determined minimum number. For example, the alert may be an icon, a textual message, and/or any suitable indication of low perfusion in the curved topographical ultrasound image slice. The perfusion analysis processor 150 may store the rendered, curved topographical ultrasound image slice having the segmented perfused areas at archive 138 and/or any suitable data storage medium.

Figure 5:
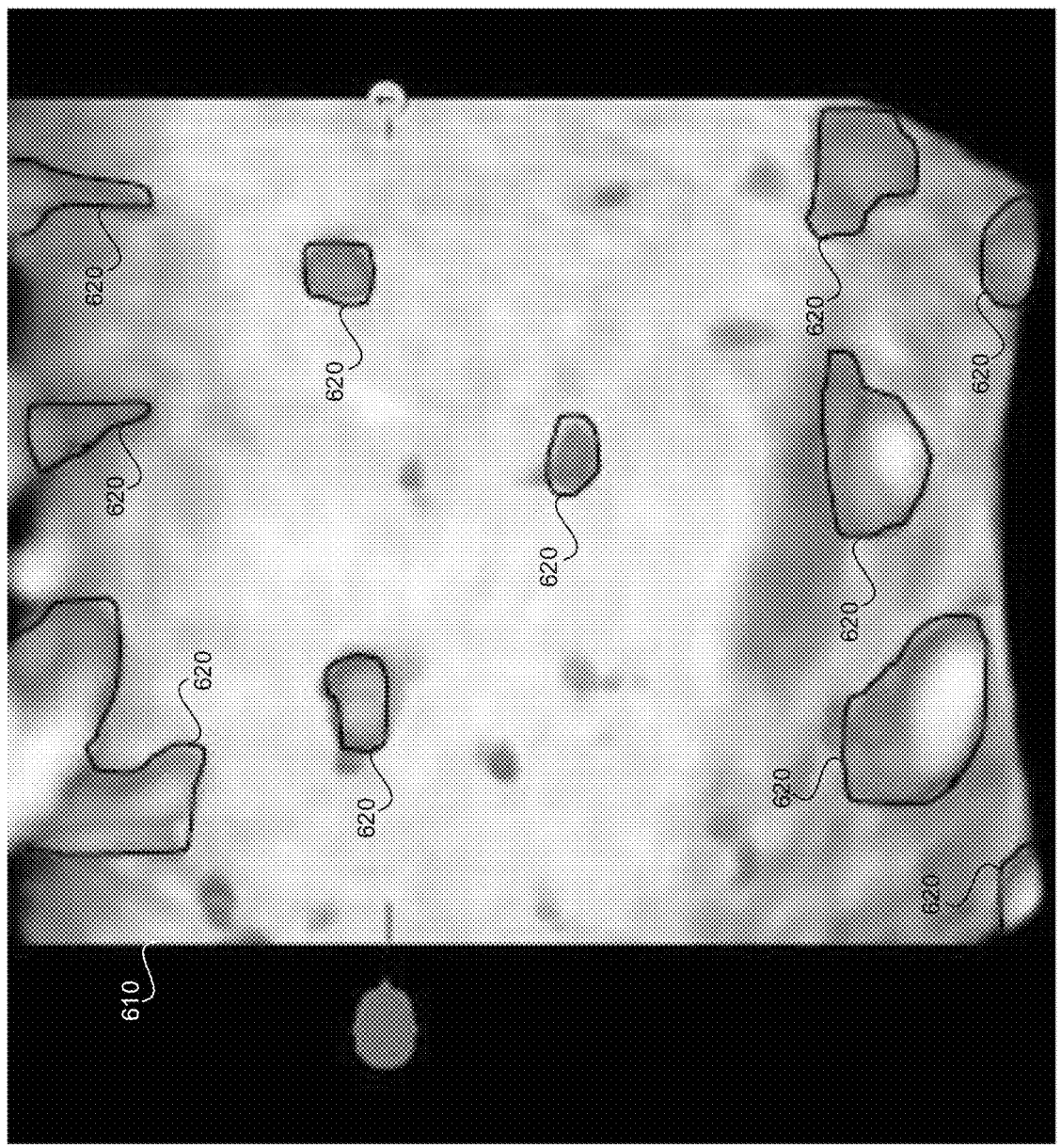
FIG. 5 is a screenshot of an exemplary volume rendering of a curved ultrasound image slice having segmented perfused areas larger than a pre-determined size threshold, in accordance with various embodiments.

FIG. 5 is a screenshot 600 of an exemplary volume rendering of a curved ultrasound image slice 610 having segmented perfused areas 620 larger than a pre-determined size threshold, in accordance with various embodiments. Referring to FIG. 5, the screenshot 600 comprises a volume rendering of a curved ultrasound image slice 610 having color Doppler information representing perfused areas 620. The rendering of the curved ultrasound image slice 610 comprises segmented perfused areas 620 larger than a pre-determined size threshold. The rendering of the curved ultrasound image slice 610 is shown with outlines of the segmented perfused areas 620. In various embodiments, the segmented perfused areas 620 may be identified by outlining, highlighting, and/or any suitable indication. In an exemplary embodiment, the perfusion analysis processor 150 may be configured to count the segmented perfused areas 620 presented on the curved topographical ultrasound image slice 610. The perfusion analysis processor 150 may be configured to provide an alert if the counted number of segmented perfused areas 620 fails to exceed a pre-determined minimum number, such as ten (10) or any suitable minimum number. For example, the screenshot 600 of the volume rendering of a curved ultrasound image slice 610 includes eleven (11) segmented perfused areas 620, which is greater than a pre-determined minimum number of ten (10) segmented perfused areas 620. If, however, the rendering of the curved ultrasound image slice 610 included less than ten (10) segmented perfused areas 620, the perfusion analysis processor 150 may be configured to provide an alert, such as an icon, textual message, and/or any suitable indication of low perfusion in the curved topographical ultrasound image slice 610.

Referring again to FIG. 1, the perfusion analysis processor 150 may be configured to cause the display system 134 to present a rendering of the curved topographical ultrasound image slice having a grid overlaid on the rendered curved topographical ultrasound image slice. The perfusion analysis processor 150 may be configured to segment perfused areas in the rendered curved topographical ultrasound image slice and automatically analyze the color Doppler information associated with the segmented perfused areas in the rendered curved topographical ultrasound image slice to provide a blood velocity measurement for each cell in the grid. The blood velocity measurement may be a peak absolute velocity, mean absolute velocity, ratio of peak positive to peak negative velocity, ratio of mean positive to mean negative velocity, and/or any suitable blood velocity measurement. The perfusion analysis processor 150 may store the rendered, curved topographical ultrasound image slice having the grid and blood velocity measurements associated with each grid cell at archive 138 and/or any suitable data storage medium.

Figure 6:
FIG. 6 is a screenshot of an exemplary volume rendering of a curved ultrasound image slice having a grid, each grid cell including a blood velocity measurement, in accordance with various embodiments.

FIG. 6 is a screenshot 700 of an exemplary volume rendering of a curved ultrasound image slice 710 having a grid 730, each grid cell including a blood velocity measurement 740, in accordance with various embodiments. Referring to FIG. 6, a screenshot 700 of a curved topographical ultrasound image slice 710 having color Doppler information representing perfused areas 720. The curved topographical ultrasound image slice 710 is overlaid with a grid 730 forming grid cells. The perfusion analysis processor 150 may be configured to segment the perfused areas 720 and perform blood velocity measurements 740 on the perfused areas 720 in each grid cell based on the color Doppler information. The perfusion analysis processor 150 may be configured to present the blood velocity measurement 740 of each grid cell in the corresponding grid cell. For example, as shown in FIG. 6, a peak absolute velocity measurement 740 is presented in each grid cell of the grid 730 superimposed on the rendering of the curved ultrasound image slice 710. In various embodiments, the blood velocity measurement may additionally and/or alternatively comprise a mean absolute velocity, ratio of peak positive to peak negative velocity, ratio of mean positive to mean negative velocity, and/or any suitable blood velocity measurement.

Referring again to FIG. 1, the perfusion analysis processor 150 may be configured to cause the display system 134 to present a rendering of the curved topographical ultrasound image slice having a grid overlaid on the rendered curved topographical ultrasound image slice. The perfusion analysis processor 150 may be configured to segment perfused areas in the rendered curved topographical ultrasound image slice and automatically analyze the color Doppler information associated with the segmented perfused areas in the rendered curved topographical ultrasound image slice to provide an area ratio measurement for each cell in the grid. The area ratio measurement may be determined by calculating a percentage of a grid cell comprising perfusion. The perfusion analysis processor 150 may be configured to highlight grid cells having an area ratio that is less than an area ratio threshold. For example, the perfusion analysis processor 150 may highlight grid cells having an area ratio below 15%. The perfusion analysis processor 150 may be configured to determine an overall perfusion insufficiency based on the number of highlighted grid cells. The perfusion analysis processor 150 may be configured to outline, tag, highlight, and/or otherwise provide an indicator of regional insufficiency by identifying a group of spatially adjacent grid cells having an area ratio below the threshold. As an example, the perfusion analysis processor 150 may provide a box around a highlighted group of spatially adjacent grid cells with an area ratio below the threshold to provide a visual indication of a low perfused regional area in the rendering of the curved topographical ultrasound image slice. The perfusion analysis processor 150 may store the rendered curved topographical ultrasound image slice having the grid, perfusion area ratio measurements associated with each grid cell, highlighting, and/or low perfusion identifiers at archive 138 and/or any suitable data storage medium.

Figure 7:
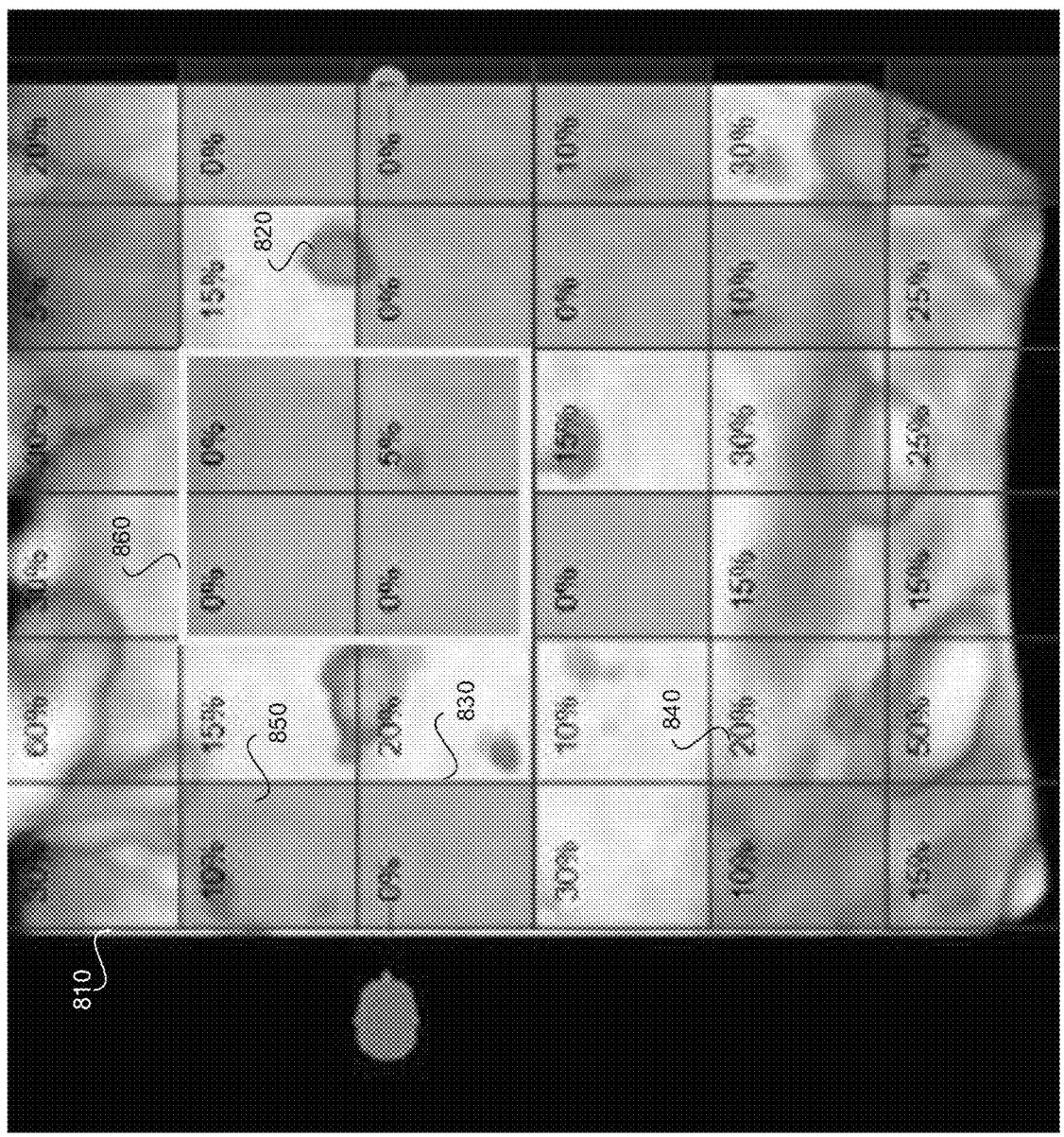
FIG. 7 is a screenshot of an exemplary volume rendering of a curved ultrasound image slice having a grid, each grid cell including a perfusion area ratio measurement, wherein grid cells having a perfusion area ratio measurement below a pre-determined threshold are highlighted, and wherein a group of spatially adjacent highlighted cells are identified, in accordance with various embodiments.

FIG. 7 is a screenshot 800 of an exemplary volume rendering of a curved ultrasound image slice 810 having a grid 830, each grid cell including a perfusion area ratio measurement 840, wherein grid cells having a perfusion area ratio measurement 840 below a pre-determined threshold are highlighted 850, and wherein a group of spatially adjacent highlighted cells 850 are identified 860, in accordance with various embodiments. Referring to FIG. 7, a screenshot 800 of a curved topographical ultrasound image slice 810 having color Doppler information representing perfused areas 820. The curved topographical ultrasound image slice 810 is overlaid with a grid 830 forming grid cells. The perfusion analysis processor 150 may be configured to segment the perfused areas 820 and perform an area ratio measurement of perfused areas 820 in each grid cell based on the color Doppler information. The perfusion analysis processor 150 may be configured to present the area ratio measurement 840 of each grid cell in the corresponding grid cell. For example, as shown in FIG. 7, an area ratio measurement 840 is presented in each grid cell of the grid 830 superimposed on the rendering of the curved ultrasound image slice 810. The perfusion analysis processor 150 may be configured to highlight 850 grid cells having an area ratio measurement 840 below an area ratio threshold, such as below 15%. The perfusion analysis processor 150 may be configured to identify 860 regional perfusion insufficiency by outlining, tagging, highlighting, and/or otherwise identifying a highlighted group 860 of spatially adjacent grid cells with an area ratio measurement below the threshold to provide a visual indication 860 of a low perfused regional area in the rendering of the curved topographical ultrasound image slice 810.

Referring again to FIG. 1, the display system 134 may be any device capable of communicating visual information to a user. For example, a display system 134 may include a liquid crystal display, a light emitting diode display, and/or any suitable display or displays. The display system 134 can be operable to present ultrasound image planes 310, 410, manipulable tools 320, 420, indications of slice thickness 330, 430, rendered topographical ultrasound image slices 520, 610, 710, 810 curved in all three dimensions and having color Doppler information, perfusion data information 620, 720, 730, 740, 820, 830, 840, 850, 860, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores ultrasound volumes, ultrasound image planes 310, 410, instructions for providing manipulable tools 320, 420, instructions for providing indications of slice thickness 330, 430, instructions for extracting topographical ultrasound image slices 520, 610, 710, 810 curved in all three dimensions and having color Doppler information, topographical ultrasound image slices 520, 610, 710, 810 curved in all three dimensions and having color Doppler information, instructions for generating perfusion data information 620, 720, 730, 740, 820, 830, 840, 850, 860, and/or perfusion data information 620, 720, 730, 740, 820, 830, 840, 850, 860, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Still referring to FIG. 1, the training system 200 may comprise a training engine 210 and a training database 220. The training engine 160 may comprise suitable logic, circuitry, interfaces and/or code that may be operable to train the neurons of the deep neural network(s) (e.g., artificial intelligence model(s)) inferenced (i.e., deployed) by the slice extraction processor 140 and/or the perfusion analysis processor 150. For example, the artificial intelligence model inferenced by the slice extraction processor 140 may be trained to automatically identify an inner surface of a placental anatomy section depicted in the ultrasound volume using database(s) 220 of classified ultrasound volumes of placental anatomy sections. As an example, the training engine 210 may train the deep neural networks deployed by the slice extraction processor 140 to automatically segment perfused areas in a topographical ultrasound image slice using database(s) 220 of classified topographical ultrasound image slices having perfused areas.

In various embodiments, the databases 220 of training images may be a Picture Archiving and Communication System (PACS), or any suitable data storage medium. In certain embodiments, the training engine 210 and/or training image databases 220 may be remote system(s) communicatively coupled via a wired or wireless connection to the ultrasound system 100 as shown in FIG. 1. Additionally and/or alternatively, components or all of the training system 200 may be integrated with the ultrasound system 100 in various forms.

Figure 8:
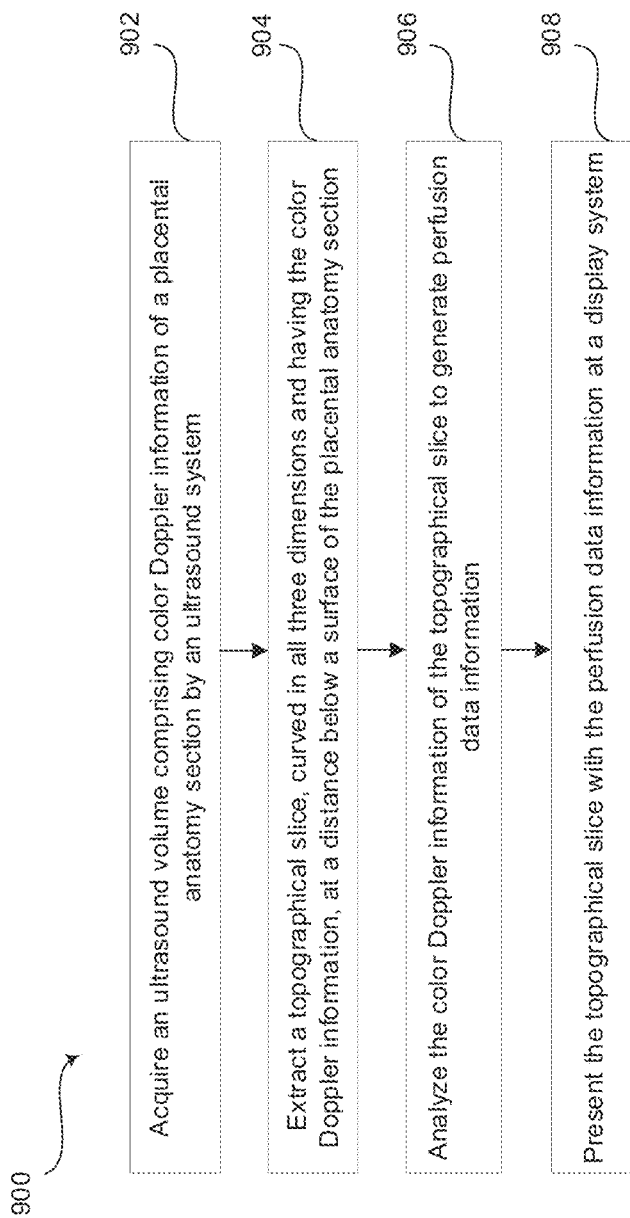
FIG. 8 is a flow chart illustrating exemplary steps that may be utilized for automatically analyzing placenta insufficiency in a curved topographical ultrasound image slice, in accordance with various embodiments.

FIG. 8 is a flow chart 900 illustrating exemplary steps 902-908 that may be utilized for automatically analyzing placenta insufficiency in a curved topographical ultrasound image slice 520, 610, 710, 810, in accordance with various embodiments. Referring to FIG. 8, there is shown a flow chart 900 comprising exemplary steps 902 through 908. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 902, an ultrasound system 100 acquires an ultrasound volume comprising color Doppler information of a placental anatomy section. For example, an ultrasound probe 104 of the ultrasound system 100 may be operated to acquire an ultrasound volume with color Doppler information of the placental anatomy section.

At step 904, a signal processor 132 of the ultrasound system 100 extracts a topographical ultrasound image slice, curved in all three dimensions and having the color Doppler information, at a distance below an inner surface of the placental anatomy section. For example, a slice extraction processor 140 of the signal processor 132 may be configured to provide tools 320, 420 presented with ultrasound planes 310, 410 of the volume at the display system 134 and manipulable to manually select a curvature of a topographical slice 520, 610, 710, 810 to be extracted from the ultrasound volume. The slice extraction processor 140 may be configured to extract and render a topographical ultrasound slice 520, 610, 710, 810 curved in all three dimensions based on the manipulated positioning of the tools 320, 420 and a defined slice thickness 330, 430. As another example, the slice extraction processor 140 may include image analysis algorithms, artificial intelligence algorithms, one or more deep neural networks (e.g., a convolutional neural network) and/or may utilize any suitable form of image analysis techniques or machine learning processing functionality configured to identify an inner surface of a placental anatomy section depicted in the ultrasound volume. The slice extraction processor 140 may be configured to automatically extract a topographical ultrasound slice curved in all three dimensions from the ultrasound volume, the topographical slice following a specified distance or depth (e.g., 5 millimeters or any suitable distance/depth) below the identified inner surface of the placental anatomy section depicted in the ultrasound volume. The slice extraction processor 140 may be configured to extract and render a topographical ultrasound slice curved in all three dimensions based on the identified inner surface, the specified distance, and a defined slice thickness (e.g., between 1-5 millimeters). The slice extraction processor 140 may be configured to present the rendered, curved topographical ultrasound image slice 520, 610, 710, 810 at the display system 134, provide the rendered, curved topographical ultrasound image slice 520, 610, 710, 810 to a perfusion analysis processor 150 of the signal processor 132, and/or store the rendered, curved topographical ultrasound image slice 520, 610, 710, 810 at archive 138 and/or any suitable data storage medium.

At step 906, the signal processor 132 of the ultrasound system 100 may analyze the color Doppler information of the topographical ultrasound image slice 520, 610, 710, 810 to generate perfusion data information 620, 720, 730, 740, 820, 830, 840, 850, 860. For example, a perfusion analysis processor 150 of the signal processor 132 may apply image analysis algorithms, artificial intelligence algorithms, one or more deep neural networks (e.g., a convolutional neural network) and/or any suitable form of image analysis techniques or machine learning processing functionality to the topographical ultrasound image slice 520, 610, 710, 810 extracted at step 904 to segment perfused areas 620, 720, 820 in the topographical image slice 520, 610, 710, 810. The perfusion data information generated by the perfusion analysis processor 150 may comprise the segmented perfused areas 620, 720, 820 larger than a pre-determined size threshold. Additionally and/or alternatively, the perfusion data information may comprise an indication of whether a counted number of segmented perfused areas exceeds a pre-determined minimum, blood velocity measurements 740 (e.g., peak absolute velocity, mean absolute velocity, ratio of peak positive to peak negative velocity, ratio of mean positive to mean negative velocity, and the like) in grid cells of a grid 730 overlaid on a topographical ultrasound image slice 520, 610, 710, 810, perfused area ratio measurements 840 (e.g., ratio of perfused area to non-perfused area) in grid cells of a grid 830 overlaid on a topographical ultrasound image slice 520, 610, 710, 810, highlighting 850, 860 of low perfusion areas, and/or any suitable indication of low perfusion areas in a topographical ultrasound image slice 520, 610, 710, 810.

At step 908, the signal processor 132 of the ultrasound system 100 may present the topographical ultrasound image slice 520, 610, 710, 810 with the perfusion data information 620, 720, 730, 740, 820, 830, 840, 850, 860 at a display system 134. For example, the perfusion analysis processor 150 of the signal processor 132 may be configured to cause the display system 134 to present the topographical ultrasound image slice 520, 610, 710, 810 extracted at step 904 with the perfusion data information 620, 720, 730, 740, 820, 830, 840, 850, 860 generated at step 906 at the display system 134.

Aspects of the present disclosure provide a method 900 and system 100 for automatically analyzing placenta insufficiency in a curved topographical ultrasound image slice 520, 610, 710, 810. In accordance with various embodiments, the method 900 may comprise acquiring 902, by an ultrasound system 100, an ultrasound volume of a placental anatomy section, the ultrasound volume comprising color Doppler information. The method 900 may comprise extracting 940, by at least one processor 132, 140 of the ultrasound system 100, a topographical ultrasound image slice 520, 610, 710, 810 at a distance below an inner surface of the placental anatomy section. The topographical ultrasound image slice 520, 610, 710, 810 is curved in all three dimensions and comprises the color Doppler information. The method 900 may comprise analyzing 906, by the at least one processor 132, 150, the color Doppler information of the topographical ultrasound image slice 520, 610, 710, 810 to generate perfusion data information 620, 720, 730, 740, 820, 830, 840, 850, 860. The method 900 may comprise causing 908, by the at least one processor 132, 140, 150, a display system 134 to present the topographical ultrasound image slice 520, 610, 710, 810 with the perfusion data information 620, 720, 730, 740, 820, 830, 840, 850, 860.

In an exemplary embodiment, the extracting 904 the topographical ultrasound image slice 520, 610, 710, 810 comprises receiving a user input manually selecting a curvature of the topographical ultrasound image slice 520, 610, 710, 810. The receiving the user input comprises presenting, by the at least one processor 132, 140, a manipulable tool 320, 420 overlaid on each of a plurality of ultrasound image planes 310, 410. The receiving the user input comprises receiving, by the at least one processor 132, 140, a manipulation of the manipulable tool 320, 420 to select the curvature of the topographical ultrasound image slice 520, 610, 710, 810. In a representative embodiment, the extracting 904 the topographical ultrasound image slice 520, 610, 710, 810 comprises automatically identifying, by the at least one processor 132, 140, the inner surface of the placental anatomy section. The extracting 904 the topographical ultrasound image slice 520, 610, 710, 810 comprises applying, by the at least one processor 132, 140, a defined distance from the inner surface of the placental anatomy section. The extracting 904 the topographical ultrasound image slice 520, 610, 710, 810 comprises applying, by the at least one processor 132, 140, a defined slice thickness 330, 430. In various embodiments, the analyzing 906 the color Doppler information of the topographical ultrasound image slice 520, 610, 710, 810 to generate perfusion data information 620, 720, 730, 740, 820, 830, 840, 850, 860 comprises segmenting, by the at least one processor 132, 150, perfused areas 620 larger than a predetermined size threshold. The analyzing 906 the color Doppler information of the topographical ultrasound image slice 520, 610, 710, 810 to generate perfusion data information 620, 720, 730, 740, 820, 830, 840, 850, 860 comprises counting, by the at least one processor 132, 150, a number of the segmented perfused areas 620. The analyzing 906 the color Doppler information of the topographical ultrasound image slice 520, 610, 710, 810 to generate perfusion data information 620, 720, 730, 740, 820, 830, 840, 850, 860 comprises providing, by the at least one processor 132, 150, an alert when the number of the segmented perfused areas 620 is less than a pre-determined minimum perfused area threshold. In certain embodiments, the analyzing 906 the color Doppler information of the topographical ultrasound image slice 520, 610, 710, 810 to generate perfusion data information 620, 720, 730, 740, 820, 830, 840, 850, 860 comprises dividing, by the at least one processor 132, 150, the topographical ultrasound image slice 520, 610, 710, 810 into a grid 730, 830. The analyzing 906 the color Doppler information of the topographical ultrasound image slice 520, 610, 710, 810 to generate perfusion data information 620, 720, 730, 740, 820, 830, 840, 850, 860 comprises determining, by the at least one processor 132, 150, the perfusion data information 620, 720, 730, 740, 820, 830, 840, 850, 860 for each grid cell of the grid 730, 830. In an exemplary embodiment, the perfusion data information 620, 720, 730, 740, 820, 830, 840, 850, 860 comprises a blood flow measurement 740 that is one or more of a peak absolute velocity, a mean absolute velocity, a ratio of peak positive to peak negative velocity, or a ratio of mean positive to mean negative velocity. In a representative embodiment, the perfusion data information 620, 720, 730, 740, 820, 830, 840, 850, 860 comprises a perfused area ratio measurement 840. The method 900 may comprise one or both of: highlighting 850, by the at least one processor 132, 150, each grid cell having the perfused area ratio measurement 840 below a pre-determined perfused area ratio measurement threshold, or identifying 860, by the at least one processor 132, 150, at least one group of spatially adjacent grid cells. Each of the spatially adjacent grid cells may comprise the perfused area ratio measurement 840 below the pre-determined perfused area ratio measurement threshold.

Various embodiments provide a system 100 for automatically analyzing placenta insufficiency in a curved topographical ultrasound image slice 520, 610, 710, 810. The system 100 may comprise an ultrasound system 100, at least one processor 132, 140, 150, and a display system 134. The ultrasound system 100 may be configured to acquire an ultrasound volume of a placental anatomy section, the ultrasound volume comprising color Doppler information. The at least one processor 132, 140 may be configured to extract a topographical ultrasound image slice 520, 610, 710, 810 at a distance below an inner surface of the placental anatomy section. The topographical ultrasound image slice 520, 610, 710, 810 is curved in all three dimensions and comprises the color Doppler information. The at least one processor 132, 150 may be configured to analyze the color Doppler information of the topographical ultrasound image slice 520, 610, 710, 810 to generate perfusion data information 620, 720, 730, 740, 820, 830, 840, 850, 860. The display system 134 may be configured to present the topographical ultrasound image slice 520, 610, 710, 810 with the perfusion data information 620, 720, 730, 740, 820, 830, 840, 850, 860.

In a representative embodiment, the at least one processor 132, 140 is configured to extract the topographical ultrasound image slice 520, 610, 710, 810 by receiving a user input manually selecting a curvature of the topographical ultrasound image slice 520, 610, 710, 810. The at least one processor 132, 140 is configured to present a manipulable tool 320, 420 overlaid on each of a plurality of ultrasound image planes 310, 410. The at least one processor 132, 140 is configured to receive a manipulation of the manipulable tool 320, 420 to select the curvature of the topographical ultrasound image slice 520, 610, 710, 810. In various embodiments, the at least one processor 132, 140 is configured to extract the topographical ultrasound image slice 520, 610, 710, 810 by automatically identifying the inner surface of the placental anatomy section. The at least one processor 132, 140 is configured to extract the topographical ultrasound image slice 520, 610, 710, 810 by applying a defined distance from the inner surface of the placental anatomy section. The at least one processor 132, 140 is configured to extract the topographical ultrasound image slice 520, 610, 710, 810 by applying a defined slice thickness 330, 430. In certain embodiments, the at least one processor 132, 150 is configured to analyze the color Doppler information of the topographical ultrasound image slice 520, 610, 710, 810 to generate perfusion data information 620, 720, 730, 740, 820, 830, 840, 850, 860 by segmenting perfused areas 620, 720, 820 larger than a predetermined size threshold. The at least one processor 132, 150 is configured to analyze the color Doppler information of the topographical ultrasound image slice 520, 610, 710, 810 to generate perfusion data information 620, 720, 730, 740, 820, 830, 840, 850, 860 by counting a number of the segmented perfused areas 620, 720, 820. The at least one processor 132, 150 is configured to analyze the color Doppler information of the topographical ultrasound image slice 520, 610, 710, 810 to generate perfusion data information 620, 720, 730, 740, 820, 830, 840, 850, 860 by providing an alert when the number of the segmented perfused areas 620, 720, 820 is less than a pre-determined minimum perfused area threshold. In an exemplary embodiment, the at least one processor 132, 150 is configured to analyze the color Doppler information of the topographical ultrasound image slice 520, 610, 710, 810 to generate perfusion data information 620, 720, 730, 740, 820, 830, 840, 850, 860 by dividing the topographical ultrasound image slice 520, 610, 710, 810 into a grid 730, 830. The at least one processor 132, 150 is configured to analyze the color Doppler information of the topographical ultrasound image slice 520, 610, 710, 810 to generate perfusion data information 620, 720, 730, 740, 820, 830, 840, 850, 860 by determining the perfusion data information 620, 720, 730, 740, 820, 830, 840, 850, 860 for each grid cell of the grid 730, 830. In a representative embodiment, the perfusion data information 620, 720, 730, 740, 820, 830, 840, 850, 860 comprises a blood flow measurement 740 that is one or more of a peak absolute velocity 740, a mean absolute velocity, a ratio of peak positive to peak negative velocity, or a ratio of mean positive to mean negative velocity. In various embodiments, the perfusion data information 620, 720, 730, 740, 820, 830, 840, 850, 860 comprises a perfused area ratio measurement 840. The at least one processor 132, 150 is configured to one or both of highlight 850 each grid cell having the perfused area ratio measurement 840 below a pre-determined perfused area ratio measurement threshold, or identify 860 at least one group of spatially adjacent grid cells. Each of the spatially adjacent grid cells comprises the perfused area ratio measurement 840 below the pre-determined perfused area ratio measurement threshold.

Certain embodiments provide a non-transitory computer readable medium having stored thereon, a computer program having at least one code section. The at least one code section is executable by a machine for causing an ultrasound system 100 to perform steps 900. The steps 900 may comprise receiving 902 an ultrasound volume of a placental anatomy section, the ultrasound volume comprising color Doppler information. The steps 900 may comprise extracting 904 a topographical ultrasound image slice 520, 610, 710, 810 at a distance below an inner surface of the placental anatomy section. The topographical ultrasound image slice 520, 610, 710, 810 is curved in all three dimensions and comprises the color Doppler information. The steps 900 may comprise analyzing 906 the color Doppler information of the topographical ultrasound image slice 520, 610, 710, 810 to generate perfusion data information 620, 720, 730, 740, 820, 830, 840, 850, 860. The steps 900 may comprise causing a display system 134 to present 908 the topographical ultrasound image slice 520, 610, 710, 810 with the perfusion data information 620, 720, 730, 740, 820, 830, 840, 850, 860.

In various embodiments, the extracting 904 the topographical ultrasound image slice 520, 610, 710, 810 comprises receiving a user input manually selecting a curvature of the topographical ultrasound image slice 520, 610, 710, 810. The receiving the user input comprises presenting a manipulable tool 320, 420 overlaid on each of a plurality of ultrasound image planes 310, 410. The receiving the user input comprises receiving a manipulation of the manipulable tool 320, 420 to select the curvature of the topographical ultrasound image slice 520, 610, 710, 810. In certain embodiments, the extracting 904 the topographical ultrasound image slice 520, 610, 710, 810 comprises automatically identifying the inner surface of the placental anatomy section. The extracting 904 the topographical ultrasound image slice 520, 610, 710, 810 comprises applying a defined distance from the inner surface of the placental anatomy section. The extracting 904 the topographical ultrasound image slice 520, 610, 710, 810 comprises applying a defined slice thickness 330, 430. In an exemplary embodiment, the analyzing 906 the color Doppler information of the topographical ultrasound image slice 520, 610, 710, 810 to generate perfusion data information 620, 720, 730, 740, 820, 830, 840, 850, 860 comprises segmenting perfused areas 620, 720, 820 larger than a predetermined size threshold. The analyzing 906 the color Doppler information of the topographical ultrasound image slice 520, 610, 710, 810 to generate perfusion data information 620, 720, 730, 740, 820, 830, 840, 850, 860 comprises counting a number of the segmented perfused areas 620, 720, 820. The analyzing 906 the color Doppler information of the topographical ultrasound image slice 520, 610, 710, 810 to generate perfusion data information 620, 720, 730, 740, 820, 830, 840, 850, 860 comprises providing an alert when the number of the segmented perfused areas 620, 720, 820 is less than a pre-determined minimum perfused area threshold. In a representative embodiment, the analyzing 906 the color Doppler information of the topographical ultrasound image slice 520, 610, 710, 810 to generate perfusion data information 620, 720, 730, 740, 820, 830, 840, 850, 860 comprises dividing the topographical ultrasound image slice 520, 610, 710, 810 into a grid 730, 830. The analyzing 906 the color Doppler information of the topographical ultrasound image slice 520, 610, 710, 810 to generate perfusion data information 620, 720, 730, 740, 820, 830, 840, 850, 860 comprises determining the perfusion data information 620, 720, 730, 740, 820, 830, 840, 850, 860 for each grid cell of the grid 730, 830. The perfusion data information 620, 720, 730, 740, 820, 830, 840, 850, 860 comprises a blood flow measurement 740 that is one or more of a peak absolute velocity 740, a mean absolute velocity, a ratio of peak positive to peak negative velocity, or a ratio of mean positive to mean negative velocity. In various embodiments, the analyzing 906 the color Doppler information of the topographical ultrasound image slice 520, 610, 710, 810 to generate perfusion data information 620, 720, 730, 740, 820, 830, 840, 850, 860 comprises dividing the topographical ultrasound image slice 520, 610, 710, 810 into a grid 730, 830. The analyzing 906 the color Doppler information of the topographical ultrasound image slice 520, 610, 710, 810 to generate perfusion data information 620, 720, 730, 740, 820, 830, 840, 850, 860 comprises determining the perfusion data information 620, 720, 730, 740, 820, 830, 840, 850, 860 for each grid cell of the grid 730, 830. The perfusion data information comprises a perfused area ratio measurement 840. The analyzing 906 the color Doppler information of the topographical ultrasound image slice 520, 610, 710, 810 to generate perfusion data information 620, 720, 730, 740, 820, 830, 840, 850, 860 comprises one or both of: highlighting 850 each grid cell having the perfused area ratio measurement 840 below a pre-determined perfused area ratio measurement threshold, or identifying 860 at least one group of spatially adjacent grid cells. Each of the spatially adjacent grid cells 860 comprises the perfused area ratio measurement 840 below the pre-determined perfused area ratio measurement threshold.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for automatically analyzing placenta insufficiency in a curved topographical ultrasound image slice.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
acquiring, by an ultrasound system, an ultrasound volume of a placental anatomy section, the ultrasound volume comprising color Doppler information;
extracting, by at least one processor of the ultrasound system, a topographical ultrasound image slice at a distance below an inner surface of the placental anatomy section, wherein the topographical ultrasound image slice is curved in all three dimensions and comprises the color Doppler information;
analyzing, by the at least one processor, the color Doppler information of the topographical ultrasound image slice to generate perfusion data information; and
causing, by the at least one processor, a display system to present the topographical ultrasound image slice with the perfusion data information.

2. The method of claim 1, wherein:
the extracting the topographical ultrasound image slice comprises receiving a user input manually selecting a curvature of the topographical ultrasound image slice; and
the receiving the user input comprises:
presenting, by the at least one processor, a manipulable tool overlaid on each of a plurality of ultrasound image planes; and
receiving, by the at least one processor, a manipulation of the manipulable tool to select the curvature of the topographical ultrasound image slice.

3. The method of claim 1, wherein the extracting the topographical ultrasound image slice comprises:

automatically identifying, by the at least one processor, the inner surface of the placental anatomy section;
applying, by the at least one processor, a defined distance from the inner surface of the placental anatomy section; and
applying, by the at least one processor, a defined slice thickness.

4. The method of claim 1, wherein the analyzing the color Doppler information of the topographical ultrasound image slice to generate perfusion data information comprises:
segmenting, by the at least one processor, perfused areas larger than a predetermined size threshold;
counting, by the at least one processor, a number of the segmented perfused areas; and
providing, by the at least one processor, an alert when the number of the segmented perfused areas is less than a pre-determined minimum perfused area threshold.

5. The method of claim 1, wherein the analyzing the color Doppler information of the topographical ultrasound image slice to generate perfusion data information comprises:
dividing, by the at least one processor, the topographical ultrasound image slice into a grid; and
determining, by the at least one processor, the perfusion data information for each grid cell of the grid.

6. The method of claim 5, wherein the perfusion data information comprises a blood flow measurement that is one or more of:
a peak absolute velocity,
a mean absolute velocity,
a ratio of peak positive to peak negative velocity, or
a ratio of mean positive to mean negative velocity.

7. The method of claim 5, wherein the perfusion data information comprises a perfused area ratio measurement, and comprising one or both of:
highlighting, by the at least one processor, each grid cell having the perfused area ratio measurement below a pre-determined perfused area ratio measurement threshold, or
identifying, by the at least one processor, at least one group of spatially adjacent grid cells, wherein each of the spatially adjacent grid cells comprises the perfused area ratio measurement below the pre-determined perfused area ratio measurement threshold.

8. A system comprising:
an ultrasound system configured to acquire an ultrasound volume of a placental anatomy section, the ultrasound volume comprising color Doppler information;
at least one processor configured to:
extract a topographical ultrasound image slice at a distance below an inner surface of the placental anatomy section, wherein the topographical ultrasound image slice is curved in all three dimensions and comprises the color Doppler information; and
analyze the color Doppler information of the topographical ultrasound image slice to generate perfusion data information; and
a display system configured to present the topographical ultrasound image slice with the perfusion data information.

9. The system of claim 8, wherein:
the at least one processor is configured to extract the topographical ultrasound image slice by receiving a user input manually selecting a curvature of the topographical ultrasound image slice; and
the at least one processor is configured to:
present a manipulable tool overlaid on each of a plurality of ultrasound image planes; and receive a manipulation of the manipulable tool to select the curvature of the topographical ultrasound image slice.

10. The system of claim 8, wherein the at least one processor is configured to extract the topographical ultrasound image slice by:
  automatically identifying the inner surface of the placental anatomy section;
  applying a defined distance from the inner surface of the placental anatomy section; and
  applying a defined slice thickness.

11. The system of claim 8, wherein the at least one processor is configured to analyze the color Doppler information of the topographical ultrasound image slice to generate perfusion data information by:
  segmenting perfused areas larger than a predetermined size threshold;
  counting a number of the segmented perfused areas; and
  providing an alert when the number of the segmented perfused areas is less than a pre-determined minimum perfused area threshold.

12. The system of claim 8, wherein the at least one processor is configured to analyze the color Doppler information of the topographical ultrasound image slice to generate perfusion data information by:
  dividing the topographical ultrasound image slice into a grid; and
  determining the perfusion data information for each grid cell of the grid.

13. The system of claim 12, wherein the perfusion data information comprises a blood flow measurement that is one or more of:
  a peak absolute velocity,
  a mean absolute velocity,
  a ratio of peak positive to peak negative velocity, or
  a ratio of mean positive to mean negative velocity.

14. The system of claim 12, wherein the perfusion data information comprises a perfused area ratio measurement, and wherein the at least one processor is configured to one or both of:
  highlight each grid cell having the perfused area ratio measurement below a pre-determined perfused area ratio measurement threshold, or
  identify at least one group of spatially adjacent grid cells, wherein each of the spatially adjacent grid cells comprises the perfused area ratio measurement below the pre-determined perfused area ratio measurement threshold.

15. A non-transitory computer readable medium having stored thereon, a computer program having at least one code section, the at least one code section being executable by a machine for causing an ultrasound system to perform steps comprising:
  receiving an ultrasound volume of a placental anatomy section, the ultrasound volume comprising color Doppler information;
  extracting a topographical ultrasound image slice at a distance below an inner surface of the placental anatomy section, wherein the topographical ultrasound image slice is curved in all three dimensions and comprises the color Doppler information;
  analyzing the color Doppler information of the topographical ultrasound image slice to generate perfusion data information; and
  causing a display system to present the topographical ultrasound image slice with the perfusion data information.

16. The non-transitory computer readable medium of claim 15, wherein:
  the extracting the topographical ultrasound image slice comprises receiving a user input manually selecting a curvature of the topographical ultrasound image slice; and
  the receiving the user input comprises:
    presenting a manipulable tool overlaid on each of a plurality of ultrasound image planes; and
    receiving a manipulation of the manipulable tool to select the curvature of the topographical ultrasound image slice.

17. The non-transitory computer readable medium of claim 15, wherein the extracting the topographical ultrasound image slice comprises:
  automatically identifying the inner surface of the placental anatomy section;
  applying a defined distance from the inner surface of the placental anatomy section; and
  applying a defined slice thickness.

18. The non-transitory computer readable medium of claim 15, wherein the analyzing the color Doppler information of the topographical ultrasound image slice to generate perfusion data information comprises:
  segmenting perfused areas larger than a predetermined size threshold;
  counting a number of the segmented perfused areas; and
  providing an alert when the number of the segmented perfused areas is less than a pre-determined minimum perfused area threshold.

19. The non-transitory computer readable medium of claim 15, wherein the analyzing the color Doppler information of the topographical ultrasound image slice to generate perfusion data information comprises:
  dividing the topographical ultrasound image slice into a grid; and
  determining the perfusion data information for each grid cell of the grid,
wherein the perfusion data information comprises a blood flow measurement that is one or more of:
  a peak absolute velocity,
  a mean absolute velocity,
  a ratio of peak positive to peak negative velocity, or
  a ratio of mean positive to mean negative velocity.

20. The non-transitory computer readable medium of claim 15, wherein the analyzing the color Doppler information of the topographical ultrasound image slice to generate perfusion data information comprises:
  dividing the topographical ultrasound image slice into a grid;
  determining the perfusion data information for each grid cell of the grid, wherein the perfusion data information comprises a perfused area ratio measurement; and one or both of:
  highlighting each grid cell having the perfused area ratio measurement below a pre-determined perfused area ratio measurement threshold, or
  identifying at least one group of spatially adjacent grid cells, wherein each of the spatially adjacent grid cells comprises the perfused area ratio measurement below the pre-determined perfused area ratio measurement threshold.

* * * * *